United States Patent [19]
Sens et al.

[11] Patent Number: 5,700,757
[45] Date of Patent: Dec. 23, 1997

[54] TRIAZOLOPYRIDINE DYES AND INTERMEDIATES THEREFOR

[75] Inventors: Rüdiger Sens, Mannheim; Helmut Reichelt; Peter Saling, both of Neustadt, all of Germany

[73] Assignee: BASF Aktiengesellschaft, Ludwigshafen, Germany

[21] Appl. No.: 597,559

[22] Filed: Feb. 2, 1996

[30] Foreign Application Priority Data

Feb. 15, 1995 [DE] Germany .................... 195 04 943.8

[51] Int. Cl.$^6$ .................... C07D 471/04; C07D 471/02
[52] U.S. Cl. .................... 503/227; 8/638; 8/643; 544/105; 544/127; 544/362; 546/119; 546/120
[58] Field of Search .................... 546/119, 120; 544/105, 127, 362; 8/638, 643; 503/227

[56] References Cited

U.S. PATENT DOCUMENTS

| | | | |
|---|---|---|---|
| 5,079,365 | 1/1992 | Sens et al. | 546/119 |
| 5,101,028 | 3/1992 | Schefczik et al. | 544/127 |
| 5,132,438 | 7/1992 | Bach et al. | 552/295 |
| 5,376,150 | 12/1994 | Lange et al. | 8/638 |

FOREIGN PATENT DOCUMENTS

| | | |
|---|---|---|
| 0 399 473 | 11/1990 | European Pat. Off. . |
| 0 413 226 | 2/1991 | European Pat. Off. . |
| 0 416 434 | 3/1991 | European Pat. Off. . |
| 0 591 736 | 4/1994 | European Pat. Off. . |
| WO 95/21219 | 8/1995 | WIPO . |
| WO 95/22581 | 8/1995 | WIPO . |

*Primary Examiner*—Richard L. Raymond
*Attorney, Agent, or Firm*—Oblon, Spivak, McClelland, Maier & Neustadt, P.C.

[57] ABSTRACT

Triazolopyridine dyes of the formula

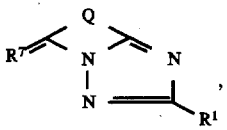

where
$R^1$ is unsubstituted or substituted $C_1$–$C_{20}$-alkyl, unsubstituted or substituted phenyl, unsubstituted or substituted hydroxyl or unsubstituted or substituted mercapto, Q is a radical of the formula

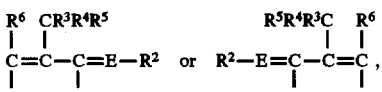

where
$R^2$ is a carbocyclic or heterocyclic radical,
$R^3$ is hydrogen or unsubstituted or substituted $C_1$–$C_4$-alkyl,
$R^4$ is hydrogen, unsubstituted or substituted $C_1$–$C_4$-alkyl or $C_1$–$C_4$-alkoxy,
$R^5$ is unsubstituted or substituted $C_1$–$C_8$-alkyl, unsubstituted or substituted phenyl, unsubstituted or substituted thienyl or unsubstituted or substituted $C_1$–$C_4$-alkoxy, or the radical $CR^3R^4R^5$ together is $C_3$–$C_7$-cycloalkyl, $C_1$–$C_4$-haloalkyl, unsubstituted or substituted phenyl or unsubstituted or substituted thienyl,
$R^6$ is cyano, carbamoyl, carboxyl, $C_1$–$C_4$-alkoxycarbonyl or benzothiazolyl, and
E is CH or nitrogen, and
$R^7$ is oxygen or a radical of an acidic—CH compound, a process for the thermal transfer of these dyes, their use for dyeing or printing synthetic materials and also triazolopyridines as intermediates for these dyes.

15 Claims, No Drawings

TRIAZOLOPYRIDINE DYES AND INTERMEDIATES THEREFOR

The present invention relates to novel triazolopyridine dyes of the formula I

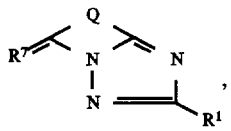
(I)

where $R^1$ is $C_1-C_{20}$-alkyl which is unsubstituted or substituted and can be interrupted by 1 to 4 oxygen atoms in ether functionalities, unsubstituted or substituted phenyl, hydroxyl, unsubstituted or substituted $C_1-C_{20}$-alkoxy, mercapto or unsubstituted or substituted $C_1-C_{20}$-alkylthio, Q is a radical of the formula

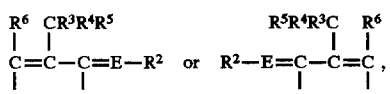

where $R^2$ is a 5- or 6-membered carbocyclic or heterocyclic radical which can be benzo-fused, $R^3$ is hydrogen or unsubstituted or substituted $C_1-C_4$-alkyl, $R^4$ is hydrogen, unsubstituted or substituted $C_1-C_4$-alkyl or $C_1-C_4$-alkoxy, $R^5$ is $C_1-C_8$-alkyl which can be interrupted by 1 or 2 oxygen atoms in ether functionalities and can be phenyl- or hydroxyl-substituted, unsubstituted or substituted phenyl, unsubstituted or substituted thienyl or $C_1-C_4$-alkoxy which can be interrupted by an oxygen atom in ether functionalities, or the radical $CR^3R^4R^5$ together is $C_3-C_7$-cycloalkyl, $C_1-C_4$-haloalkyl, unsubstituted or substituted phenyl or unsubstituted or substituted thienyl, $R^6$ is cyano, carbamoyl, carboxyl, $C_1-C_4$-alkoxycarbonyl or benzothiazolyl, and E is CH or nitrogen, and $R^7$ is oxygen or a radical of the formula

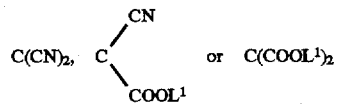

where $L^1$ is in each case $C_1-C_8$-alkyl which can be interrupted by 1 or 2 oxygen atoms in ether functionalities, to a process for the thermal transfer of these dyes, to their use for dyeing or printing synthetic materials and also to traizolopyridines as intermediates for these dyes.

U.S. Pat. No. 5,079,365 and WO-A-95/22581 disclose triazolopyridine dyes which carry a different substituent in ring position 4 of the pyridine ring.

It is an object of the present invention to provide novel triazolopyridine dyes having a different chemical structure and advantageous properties. They shall be simple to synthesize.

We have found that this object is achieved by the triazolopyridine dyes of the formula I defined at the outset.

The dyes of the formula I may occur in a plurality of tautomeric forms, all of which are embraced by the claims. For example, the compounds with $R^3$=hydrogen and $R^7$=oxygen may occur in the following tautomeric forms, inter alia:

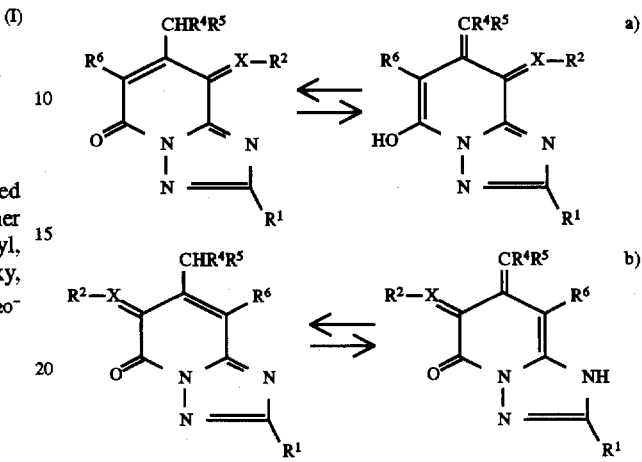

$R^2$ is a 5- or 6-membered carbocyclic or heterocyclic radical which is unsubstituted or substituted and can be benzo-fused.

$R^2$ radicals may be derived, for example, from components from the benzene, indole, quinoline, aminonaphthalene, pyrrole, aminothiazole, benzimidazole, benzothiazole, aminothiophene or diaminopyridine series.

Examples of important $R^2$ radicals are those of the formulae IIa to IIj

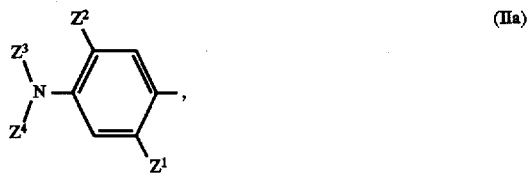
(IIa)

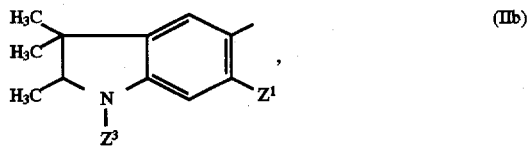
(IIb)

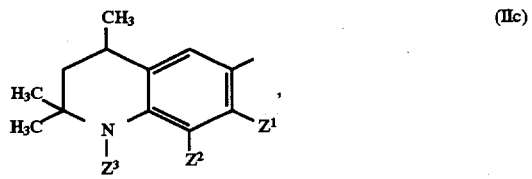
(IIc)

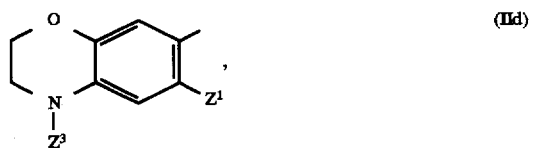
(IId)

-continued

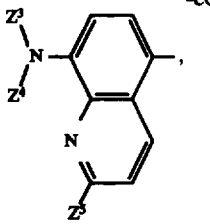
(IIe)

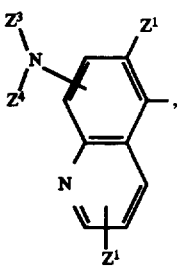
(IIf)

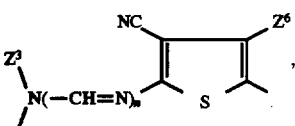
(IIg)

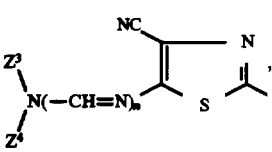
(IIh)

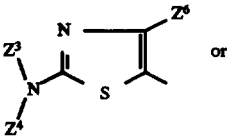
(IIi)

or

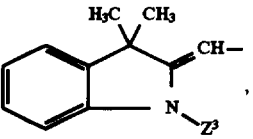
(IIj)

where n is 0 or 1, $Z^1$ is hydrogen, $C_1$–$C_8$-alkyl which can be interrupted by 1 or 2 oxygen atoms in ether functionalities, hydroxyl, $C_1$–$C_4$-alkoxy, especially methoxy or ethoxy, formylamino, $C_1$–$C_4$-alkylsulfonylamino, $C_1$–$C_4$-mono- or dialkylaminosulfonylamino or the radical —NHCOZ$^7$ or —NHCOZ$^7$ or —NHCO$_2$Z$^7$ where Z$^7$ is phenyl, benzyl, tolyl or $C_1$–$C_8$-alkyl which can be interrupted by 1 or 2 oxygen atoms in ether functionalities, $Z^2$ is hydrogen, $C_1$–$C_4$-alkyl, especially methyl, or $C_1$–$C_4$-alkoxy, especially methoxy or ethoxy, $Z^3$ and $Z^4$ are each independently of the other hydrogen, $C_1$–$C_8$-alkyl which is unsubstituted or substituted and can be interrupted by 1 or 2 oxygen atoms in ether functionalities, $C_3$–$C_4$-alkenyl, $C_5$–$C_7$-cycloalkyl, unsubstituted or substituted phenyl or, together with the nitrogen atom connecting them, a 5- or 6-membered saturated heterocyclic radical which may contain further hetero atoms, $Z^5$ is hydrogen or $C_1$–$C_4$-alkyl, especially methyl, and $Z^6$ is hydrogen, halogen, $C_1$–$C_8$-alkyl, unsubstituted or substituted phenyl, unsubstituted or substituted benzyl, cyclohexyl, thienyl, hydroxyl, $C_1$–$C_4$-alkoxy, $C_1$–$C_4$-alkylthio or $C_1$–$C_8$-monoalkylamino.

All the alkyl and alkenyl groups occurring in the abovementioned formulae can be either straight-chain or branched.

Examples of suitable substituents in substituted alkyl radicals in the abovementioned formulae are unsubstituted or substituted phenyl, unsubstituted or substituted phenoxy, carboxyl, $C_1$–$C_{20}$-alkoxycarbonyl whose alkyl chain can be interrupted by 1 to 4 oxygen atoms in ether functionalities and substituted by phenyl or phenoxy, or hydroxyl, halogen, cyano, $C_1$–$C_6$-alkanoyloxy, $C_1$–$C_4$-alkylaminocarbonyloxy or $C_1$–$C_4$-alkoxycarbonyloxy, where in the latter case the alkoxy group can be substituted by phenyl or $C_1$–$C_4$-alkoxy. Moreover, as a rule, the alkyl radicals have 1 to 3 substituents.

Where the abovementioned formulae contain alkyl radicals which are interrupted by oxygen atoms in ether functionalities, the preferred alkyl radicals are interrupted by 1 or 2 oxygen atoms in ether functionalities.

Examples of suitable substituents for substituted phenyl or thienyl radicals in the abovementioned formulae are $C_1$–$C_4$-alkyl, trifluoromethyl, $C_1$–$C_4$-alkoxy, halogen, nitro or carboxyl. Moreover, as a rule, the phenyl or thienyl radicals have 1 to 3 substituents.

Examples of suitable $L^1$, $R^1$, $R^3$, $R^4$, $R^5$, $Z^1$, $Z^2$, $Z^3$, $Z^4$, $Z^5$, $Z^6$ and $Z^7$ radicals are methyl, ethyl, propyl, isopropyl, butyl, isobutyl, sec-butyl or tert-butyl, as well as the $L^2$ and $L^3$ radicals mentioned below.

Further examples of $L^1$, $R^1$, $R^5$, $Z^1$, $Z^3$, $Z^4$, $Z^6$ and $Z^7$ radicals are pentyl, isopentyl, neopentyl, tert-pentyl hexyl, 2-methylpentyl, heptyl, octyl, 2-ethylhexyl or isooctyl.

Further examples of $R^1$ radicals are nonyl, isononyl, decyl, isodecyl, undecyl, dodecyl, tridecyl, isotridecyl, tetradecyl, pentadecyl, hexadecyl, heptadecyl, octadecyl, nonadecyl or eicosyl. (The names isooctyl, isononyl, isodecyl and isotridecyl are trivial names derived from the alcohols obtained from the oxo process (cf. in this connection Ullmann's Encyclopedia of industrial Chemistry, 5th edition, Vol. A1, pages 290 to 293, and Vol. A 10, pages 284 and 285)).

Further examples of $L^1$, $R^1$, $R^5$, $Z^1$, $Z^3$, $Z^4$ and $Z^7$ radicals are 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-butoxybutyl 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl or 4,8-dioxadecyl.

Further examples of $R^1$ radicals are 3,6,9-trioxadecyl, 3,6,9-trioxaundecyl, 3,6,9,12-tetraoxatridecyl, 3,6,9,12-tetraoxatetradecyl, methylthio, ethylthio, propylthio, isopropylthio, butylthio, isobutylthio, sec-butylthio, pentylthio, isopentylthio, neopentylthio, tert-pentylthio, hexylthio, heptylthio, 1-ethylpentylthio, octylthio, isooctylthio, 2-ethylhexylthio, nonylthio, isononylthio, decylthio, isodecylthio, undecylthio, dodecylthio, tridecylthio, isotridecylthio, tetradecylthio, pentadecylthio, hexadecylthio, heptadecylthio, octadecylthio, nonadecylthio or eicosylthio.

Further examples of $R^1$, $R^5$, $Z^3$, $Z^4$ and $Z^6$ radicals, and of the radical $CR^3R^4R^5$ together, are phenyl, 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2,4-dimethylphenyl, 2-, 3- or 4-methoxyphenyl, 2-, 3- or 4-ethoxyphenyl, 2-, 3- or 4-isobutoxyphenyl, 2,4-dimethoxyphenyl, 2-, 3- or 4-fluorophenyl, 2-, 3- or 4-chlorophenyl, 2-, 3- or 4-trifluoromethylphenyl, 2-, 3- or 4-nitrophenyl or 2-, 3- or 4-carboxyphenyl.

Further examples of $R^1$, $R^3$, $R^4$, $Z^3$ and $Z^4$ radicals are 2-carboxyethyl, 2-methoxycarbonylethyl, benzyl, 1- or 2-phenylethyl, 2-, 3- or 4-methylbenzyl, 2-, 3- or 4-methoxybenzyl, 2-, 3- or 4-chlorobenzyl, 2-, 3- or 4-nitrobenzyl, 3-benzyloxypropyl, phenoxymethyl, 6-phenoxy-4-oxahexyl, 8-phenoxy-4-oxaoctyl, 2-hydroxyethyl, 2- or 3-hydroxypropyl, fluoromethyl, chloromethyl, difluoromethyl, dichloromethyl, trifluoromethyl, trichloromethyl, 2-fluoroethyl, 2-chloroethyl, 2,2,2-trifluoroethyl, pentafluoroethyl, heptafluoropropyl, nonafluorobutyl, 2-cyanoethyl, 2- or 3-cyanopropyl, 2-acetyloxyethyl, 2- or 3-acetyloxypropyl, 2-isobutyryloxyethyl, 2- or 3-isobutyryloxypropyl, 2-methoxycarbonylethyl, 2- or 3-methoxycarbonylpropyl, 2-ethoxycarbonylethyl, 2- or 3-ethoxycarbonylpropyl, 2-methylaminocarborryloxyethyl, 2-methoxycarbonyloxyethyl, 2- or 3-methoxycarbonyloxypropyl, 2-ethoxycarbonyloxyethyl, 2- or 3-ethoxycarbonyloxypropyl, 2-butoxycarbonyloxyethyl, 2- or 3-butoxycarbonyloxypropyl, 2-(2-phenylethoxycarbonyloxy)ethyl, 2- or 3-(2-phenylethoxycarbonyloxy)propyl, 2-(2-ethoxyethoxycarbonyloxy)ethyl or 2- or 3-(2-ethoxyethoxycarbonyloxY)propyl.

Further examples of $R^5$ are methoxymethyl, ethoxymethyl, propoxymethyl, butoxymethyl, benzyl, 1- or 2-phenylethyl, hydroxymethyl, 1- or 2-hydroxyethyl, 1-, 2- or 3-hydroxypropyl or 4-hydroxy-2-oxabutyl.

Further examples of $R^5$ and $CR^3R^4R^5$ are thien-2-yl, thien-3-yl, 3- or 4-methylthienyl or 3- or 4-fluorothienyl.

Further examples of $CR^3R^4R^5$ are fluoromethyl, chloromethyl, difluoromethyl, dichloromethyl, trifluoromethyl, trichloromethyl, 2-fluoroethyl, 2-chloroethyl, 2,2,2-trifluoroethyl, pentafluoroethyl, heptafluoropropyl, nonafluorobutyl, cyclopropyl, cyclobutyl, cyclopentyl, methylcyclopentyl, cyclohexyl, methylcyclohexyl or cycloheptyl.

Further examples of $Z^3$ and $Z^4$ radicals are cyclopentyl, methylcyclopentyl, cyclohexyl, methylcyclohexyl, cycloheptyl, allyl or methallyl.

Examples of $Z^1$ radicals are methylsulfonylamino, ethylsulfonylamino, propylsulfonylamino, isopropylsulfonylamino, butylsulfonylamino, mono- or dimethylaminosulfonylamino, mono- or diethylaminosulfonylamino, mono-, or dipropylaminosulfonylamino, mono- or diisopropylaminosulfonylamino, mono- or dibutylaminosulfonylamino or (N-methyl-N-ethylaminosulfonyl)amino.

Further examples of $Z^6$ radicals are fluorine, chlorine, bromine, benzyl, 2-methylbenzyl, 2,4-dimethylbenzyl, 2-methoxybenzyl, 2,4-dimethoxybenzyl, methylamino, ethylamino, propylamino, isopropylamino, butylamino, pentylamino, hexylamino, heptylamino, octylamino, 2-ethylhexylamino, methylthio, ethylthio, propylthio, isopropylthio or butylthio.

Further examples of $R^1$, $R^4$, $R^5$, $Z^1$, $Z^2$ and $Z^6$ radicals are methoxy, ethoxy, propoxy, isopropoxy, butoxy, isobutoxy, sec-butoxy or tert-butoxy.

Further examples of $R^1$ are pentyloxy, isopentyloxy, neopentyloxy, tert-pentyloxy, hexyloxy, heptyloxy, 1-ethylpentyloxy, octyloxy, isooctyloxy, 2-ethylhexyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, nonadecyloxy or eicosyloxy.

When $Z^3$ and $Z^4$ or the below-mentioned $L^2$ and $L^3$ radicals together with the nitrogen atom connecting them form a 5- or 6-membered saturated heterocyclic radical which may have further hetero atoms, suitable examples thereof are pyrrolidinyl, piperidinyl, morpholinyl, piperazinyl or N-($C_1$–$C_4$-alkyl)piperazinyl.

Examples of $R^6$ radicals are methoxycarbonyl, ethoxycarbonyl, propoxycarbonyl, isopropoxycarbonyl, butoxycarbonyl, isobutoxycarbonyl or sec-butoxycarbonyl.

Preferred triazolopyridine dyes of the formula I are those where $R^6$ is cyano.

Further preferred triazolopyridine dyes of the formula I are those where $R^5$ is $C_1$–$C_5$-alkyl or phenyl.

Preference is further given to triazolopyridine dyes of the formula I where the radical $CR^3R^4R^5$ together is unsubstituted or substituted phenyl or unsubstituted or substitued thienyl.

Further preferred triazolopyridine dyes of the formula I are those where $R^1$ is $C_1$–$C_{13}$-alkyl which is unsubstituted or substituted by $C_1$–$C_6$-alkanoyloxy, $C_1$–$C_8$-alkoxycarbonyl whose alkyl chain can be interrupted by 1 or 2 oxygen atoms in ether functionalities, phenyl or $C_1$–$C_4$-alkylphenyl, and which can be interrupted by 1 or 2 oxygen atoms in ether functionalities, or unsustituted or substituted phenyl.

Particularly preferred triazolopyridine dyes of the formula I are those where $R^1$ is alkyl, alkoxyalkyl, alkanoyloxyalkyl or alkoxycarbonylalkyl, each of these radicals having up to 12 carbon atoms, unsubstituted or methyl-substituted benzyl or unsubstituted or methyl-substituted phenyl.

Further particularly preferred triazolopyridine dyes of the formula I are those where $R^2$ is a radical of the abovementioned formula IIa, IIc, IIg or IIi, where $Z^1$ is hydrogen, $C_1$–$C_4$-alkyl, $C_1$–$C_4$-alkoxy or $C_1$–$C_8$-alkanoylamino, $Z^2$ is hydrogen, methyl, methoxy or ethoxy, $Z^3$ and $Z^4$ are each, independently of one another, alkyl, alkoxyalkyl, alkanoyloxyalkyl or alkoxycarbonylalkyl, each of these radicals having up to 12 carbon atoms, hydrogen, unsubstituted or methyl-substituted benzyl or phenyl and $Z^6$ is hydrogen, $C_1$–$C_8$-alkyl, unsubstituted or $C_1$–$C_4$-alkyl- or $C_1$–$C_4$-alkoxy-substituted phenyl, benzyl or thienyl.

The dyes of the formula I according to the invention can be prepared by conventional methods.

For example, those triazolopyridine dyes of the formula I where E is CH can be obtained by condensing aldehydes of the formula III $$R^2\text{—CHO} \qquad\qquad (III),$$

where $R^2$ has the abovementioned meaning, with triazolopyridines of the formula IVa or IVb

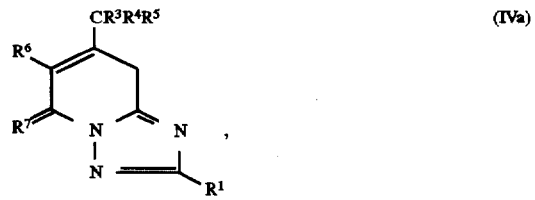
(IVa)

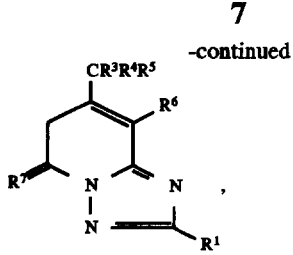
(IVb)

where $R^1$, $R^3$, $R^4$, $R^5$, $R^6$ and $R^7$ each have the abovementioned meanings.

Those triazolopyridine dyes of the formula I where E is nitrogen can be obtained, for example, by condensing nitroso compounds of the formula V

 (V), where $R^2$ has the abovementioned meaning, or by oxidative coupling of amino compounds of the formula VI

 (VI), where $R^2$ has the abovementioned meaning, with the triazolopyridines IVa or IVb.

However, it is also possible to prepare the novel dyes of the formula I in the manner known from WO-A-95/21219, for example by condensing a compound of the formula IVc or IVd

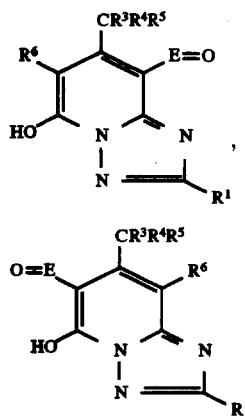

where E, $R^1$, $R^3$, $R^4$, $R^5$ and $R^6$ are each as defined above, with a compound of the formula VII

 (VII), where $R^2$ is as defined above.

The present invention further provides novel triazolopyridines of the formula IV

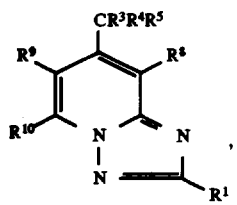

where $R^1$ is $C_1-C_{20}$-alkyl which is unsubstituted or substituted and can be interrupted by 1 to 4 oxygen atoms in ether functionalities, unsubstituted or substituted phenyl, hydroxyl, unsubstituted or substituted $C_1-C_{20}$-alkoxy, mercapto or unsubstituted or substituted $C_1-C_{20}$-alkylthio, $R^3$ is hydrogen or unsubstituted or substituted $C_1-C_4$-alkyl, $R^4$ is hydrogen or unsubstituted or substituted $C_1-C_4$-alkyl or $C_1-C_4$-alkoxy, $R^5$ is $C_1-C_8$-alkyl which can be interrupted by 1 or 2 oxygen atoms in ether functionalities and can be phenyl- or hydroxyl-substituted, unsubstituted or substituted phenyl, unsubstituted or substituted thienyl or $C_1-C_4$-alkoxy which can be interrupted by an oxygen atom in ether functionalities, or the radical $CR^3R^4R^5$ together is $C_3-C_7$-cycloalkyl, $C_1-C_4$-haloalkyl, unsubstituted or substituted phenyl or unsubstituted or substituted thienyl, $R^8$ is hydrogen, formyl, nitroso, cyano, $C_1-C_4$-alkoxymethyl or a radical of the formula $CH_2-NL^2L^3$, where $L^2$ and $L^3$ are each independently of the other hydrogen or $C_1-C_4$-alkyl which can be interrupted by $C_1-C_4$-alkylimino, or together with the nitrogen atom connecting them are a 5- or 6-membered saturated heterocyclic radical, $R^9$ is hydrogen, cyano, carbamoyl, carboxyl, $C_1-C_4$-alkoxycarbonyl or benzothiazolyl, and $R^{10}$ is hydroxyl, mercapto, halogen, the radical $-NL^2L^3$, where $L^2$ and $L^3$ are each as defined above, or the radical of an acidic—CH compound.

The exact IUPAC name for the basic structure underlying the novel triazolopyridines of the formula I is 1,2,4-triazolo[1,5-a]pyridine, the rings being numbered as follows:

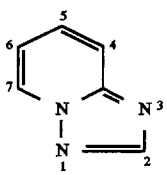

The compounds of the formula IV can occur in a plurality of tautomeric forms, all of which are embraced by the claims. For example, the compounds with $R^{10}$=hydroxyl can occur inter alia in the following tautomeric forms:

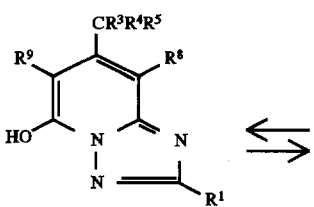

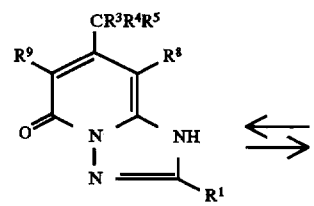

9

-continued

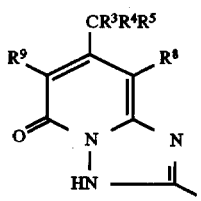

If $R^{10}$ in the formula IV is a radical of an acidic—CH compound, this radical can derive for example from nitromethane, nitroethane or from acidic—CH compounds of the formulae VIII to XIII

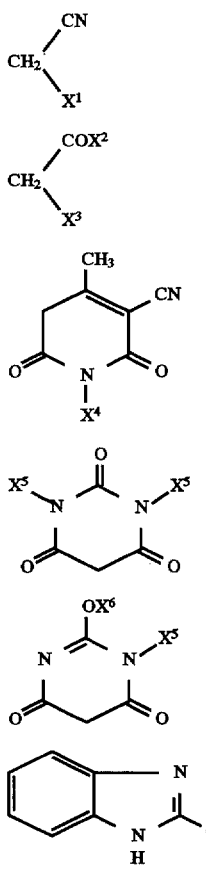

where
$X^1$ is cyano, nitro, $C_1$–$C_4$-alkanoyl, unsubstituted or $C_1$–$C_4$-alkyl-, $C_1$–$C_4$-alkoxy- or halogen-substituted benzoyl, $C_1$–$C_4$-alkylsulfonyl, unsubstituted or $C_1$–$C_4$-alkyl-, $C_1$–$C_4$-alkoxy- or halogen-substituted phenylsulfonyl, carboxyl, $C_1$–$C_4$-alkoxycarbonyl, phenoxycarbonyl, carbamoyl, mono-or di($C_1$–$C_4$-alkyl)carbamoyl, unsubstsituted or $C_1$–$C_4$-alkyl-, $C_1$–$C_4$-alkoxy- or halogen-substituted phenylcarbamoyl, unsubstituted or $C_1$–$C_4$-alkyl-, $C_1$–$C_4$-alkoxy-, halogen- or nitro-substituted phenyl, benzothiazol-2-yl, benzimidazol-2-yl, 5-phenyl-1,3,4-thiadiazol-2-yl or 2-hydroxyquinoxalin-3-yl, $X^2$ is $C_1$–$C_4$-alkyl or $C_1$–$C_4$-alkoxy, $X^3$ is $C_1$–$C_4$-alkoxycarbonyl, phenylcarbamoyl or benzimidazol-2-yl, $X^4$ is hydrogen or $C_1$–$C_6$-alkyl, $X^5$ is hydrogen, $C_1$–$C_4$-alkyl or phenyl, and

10

$X^6$ is $C_1$–$C_4$-alkyl.

Of particular interest are acidic—CH compounds of the formula VIII, IX or XI where $X^1$ is cyano, acetyl, benzoyl, $C_1$–$C_4$-alkoxycarbonyl, phenoxycarbonyl, $C_1$–$C_2$-monoalkylcarbonyl, phenylcarbamoyl, phenyl, benzimidazol-2-yl, benzothiazol-2-yl or 5-phenyl-1,3,4-thiazol-2-yl, $X^2$ is $C_1$–$C_2$-alkoxy, $X^3$ is $C_1$–$C_2$-alkoxycarbonyl or phenylcarbamoyl, and $X^5$ is methyl.

Examples of $R^8$ are aminomethyl, N-mono- or N,N-dimethylaminomethyl, N-mono- or N,N-diethylaminomethyl, N-mono- or N,N-dipropylaminomethyl, pyrrolidinomethyl, piperidinomethyl, morpholinomethyl, piperazinomethyl, N-($C_1$–$C_4$-alkyl) piperazinomethyl, methoxymethyl, ethoxymethyl, propoxymethyl, isopropoxymethyl or butoxymethyl.

Further exemplifications of radicals which occur in the formula IV can be taken from the above observations.

Preference is given to triazolopyridines of the formula IV where one of the two radicals $R^8$ and $R^9$ is hydrogen and the other is cyano.

Preference is further given to triazolopyridines of the formula IV where $R^9$ is cyano.

Preference is further given to triazolopyridines of the formula IV where $R^5$ is $C_1$–$C_5$-alkyl or phenyl.

Preference is further given to triazolopyridines of the formula IV where the radical $CR^3R^4R^5$ together is unsubstituted or substituted phenyl or unsubstituted or substituted thienyl.

Preference is further given to triazolopyridines of the formula IV where $R^1$ is $C_1$–$C_{13}$-alkyl or phenyl.

Particular preference is given to triazolopyridines of the formula IV where $R^9$ is cyano and $R^8$ is hydrogen.

The triazolopyridines, of the formula IV, according to the present invention can be prepared by conventional methods as described for example in U.S. Pat. No. 5,101,028.

For example, the triazolopyridines of the formula IVe

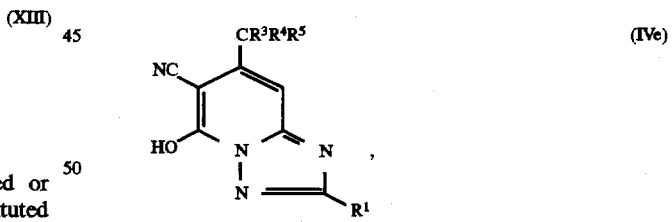

where $R^1$, $R^3$, $R^4$ and $R^5$ are each as defined above, can be prepared by reacting an aminonitrile of the formula XIV

where $R^3$, $R^4$ and $R^5$ are each as defined above, with a hydrazine of the formula XV

where A is amino or the abovementioned radical $R^1$.

Those triazolopyridines of the formula IVf

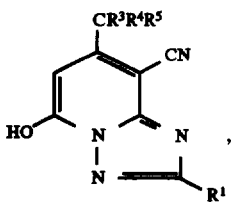 (IVf)

where $R^1$, $R^3$, $R^4$ and $R^5$ are each as defined above, can be prepared for example by reacting a hydrazine of the formula XVI $$A-CO-NH-NH-CO-CH_2COCR^3R^4R^5 \qquad (XVI),$$

where A, $R^3$, $R^4$ and $R^5$ are each as defined above, with malonitrile.

The other triazolopyridines of the formula IV can be prepared from the compounds of the formula IVe or IVf in a conventional manner.

For example, the substituent $R^8$ can be introduced by means of an electrophilic substitution reaction, for example a Vilsmeier reaction, or nitrosation, if appropriate with subsequent derivatization.

The cyano group in position 4 or 6 can be converted into the carbamoyl, carboxyl or $C_1$–$C_4$-alkoxycarbonyl group in a conventional manner.

The hydroxyl group in position 7 can be replaced with halogen by treatment with acid halides, in particular acid chlorides, for example phosphoryl chloride.

The halogen atom in turn can be replaced with acidic—CH compounds, amines of the formula XVII

 (XVII)

where $L^2$ and $L^3$ are each as defined above, or hydrogen sulfide in a conventional manner.

The novel triazolopyridines of the formula IV are useful intermediates, in particular for the synthesis of the dyes of the formula I.

The present invention further provides a process for transferring dyes from a support to a plastic-coated paper by diffusion or sublimation with the aid of an energy source, which comprises using a support on which there is or are one or more triazolopyridine dyes of the formula I.

To prepare the dye supports (transfers) required for the process according to the invention, the dyes of the formula I are processed in a suitable organic solvent or in mixtures of solvents with one or more binders, with or without the addition of auxiliaries, to a printing ink. The latter preferably contains the dyes of the formula I in the form of a molecular disperse solution. The printing ink can be applied by means of a knife to the inert support, and the dye can be dried, for example, in the air or with a hair dryer. Examples of suitable organic solvents for the dyes of the formula I are those in which the solubility of the dyes of the formula I is more than 1% by weight, preferably more than 5% by weight, at 20° C.

Examples which may be mentioned are ethanol, propanol, isobutanol, tetrahydrofuran, methylene chloride, methyl ethyl ketone, cyclopentanone, cyclohexanone, toluene, chlorobenzene or mixtures thereof.

Suitable binders are all resins or polymeric materials which are soluble in organic solvents and which are able to bind the dyes to the inert support in a manner resistant to abrasion. The binders preferred for this are those which take up the dye mixture in the form of a clear transparent film after the printing ink has dried in the air, without visible crystallization of the dye mixture occurring.

Examples of such binders are mentioned in U.S. Pat. No. 5,132,438 or the relevant patent applications cited therein. Mention may also be made of saturated linear polyesters. Preferred binders are ethylcellulose, ethylhydroxyethylcellulose, polyvinylbutyral, polyvinyl acetate, cellulose propionate or saturated linear polyesters.

The binder:dye ratio by weight is generally from 1:1 to 10:1.

Examples of suitable auxiliaries are release agents as mentioned in U.S. Pat. No. 5,132,438 or the relevant patent applications cited therein. In addition, particular mention should be made of organic additives which prevent the transfer dyes crystallizing out on storage or on heating of the ink ribbon, eg. cholesterol or vanillin.

Examples of suitable inert supports are described in U.S. Pat. No. 5,132,438 or the relevant patent applications cited therein. The thickness of the support is generally from 3 to 30 μm.

Suitable for use as dye recipient layer are in principle all temperature-stable plastic layers with affinity for the dyes to be transferred, for example modified polycarbonates or polyesters. Further details of this may be found, for example, in U.S. Pat. No. 5,132,438 or the relevant patent applications cited therein.

The transfer takes place by means of an energy source, for example by means of a laser or a thermal head, it being necessary that the latter be heatable to $\geq 300°$ C. so that the dye transfer can take place in a time in the range $0<t<15$ msec. During this, the dye migrates out of the transfer sheet and diffuses into the surface coating of the recipient medium.

The dyes of the formula I according to the invention have advantageous technical properties in the transfer thereof. They display a high solubility in the ink ribbon (good compatibility with the binder), a high stability in the printing ink, a good transferability, a high image stability (ie. good fastness to light and good stability to environmental effects, eg. moisture, temperature or chemicals) and permit flexible color adaptation to preexistent subtractive primary colors in the sense of optimal trichromatic printing (maximum possible brilliance of primary or mixed colors and deep neutral black).

The dyes of the formula I according to the invention are furthermore suitable and advantageous for dyeing or printing synthetic materials, eg. polyesters, polyamides or polycarbonates. Particular mention should be made of materials in textile form, such as fibers, yarns, threads, knits, wovens or nonwovens made of polyester or polyamide or polyester/cotton blends. They are further suitable for dyeing keratinous fibers, e.g. hairs or furs.

The novel dyes of the formula I are further suitable for producing color filters as described, for example, in EP-A 399 473.

Finally, they can also be used advantageously as colorants for producing toners for electrophotography.

The following examples illustrate the invention.

A) Preparation of Triazolopyridines

EXAMPLE 1

In a 1 l flask a solution of 50 g (1 mol) of hydrazine hydrate in 200 ml of N,N-dimethylacetamide was admixed at a temperature of from 40° to 50° C. with 124.45 g (1.1 mol) of ethyl cyanoacetate and the mixture was stirred at from 40° to 50° C. for 1 h. Then 101 g (1 mol) of triethylamine were added. Finally 161.9 g (1 mol) of 2-ethylhexanoyl chloride were added at 30° C. over 4 h and the mixture was subsequently stirred at 30° C. for 2 h. Then 1 g of titanium tetraethoxide and 123 g (1.5 mol) of the compound of the formula

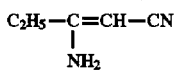

were added, and the mixture was heated to 120° C. to distill the resulting ethanol off. The mixture was subsequently stirred for 1 h and then heated to 160° C. for 6 h. The reaction mixture was then poured into a hot solution at 70° C. of 150 ml of concentrated hydrochloric acid and 2 l of water, and the mixture was stirred at 70° C. for 1 h then filtered with suction. The residue was washed with 2 l of water and dried under reduced pressure to leave 198 g of the compound of the formula

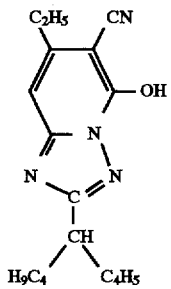

purity (HPLC): 75%

EXAMPLE 2

In a 1 l flask a solution of 50 g (1 mol) of hydrazine hydrate in 200 ml of N,N-dimethylacetamide was admixed at a temperature of from 40° to 50° C. with 124.45 g (1.1 mol) of ethyl cyanoacetate and the mixture was stirred at from 40° to 50° C. for 1 h. Then 101 g (1 mol) of triethylamine were added. Finally 161.9 g (1 mol) of 2-ethylhexanoyl chloride were added at 30° C. over 4 h and the mixture was subsequently stirred at 30° C. for 2 h. Then 1 g of titanium tetraethoxide and 123 g (1.5 mol) of the compound of the formula

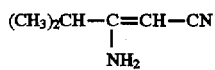

were added, and the mixture was heated to 120° C. to distill the resulting ethanol off. The mixture was subsequently stirred for 1 h and then heated to 160° C. for 6 h. The reaction mixture was then poured into a hot solution at 70° C. of 150 ml of concentrated hydrochloric acid and 2 l of water, and the mixture was stirred at 70° C. for 1 h then filtered with suction. The residue was washed with 2 l of water and dried under reduced pressure to leave 153 g of the compound of the formula

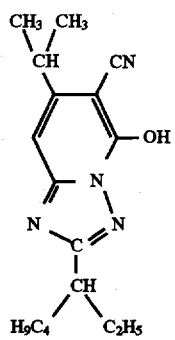

purity (HPLC): 79%

The same method can be used to prepare the triazolopyridines listed below in Table 1.

TABLE 1

| Ex. No. | $R^1$ | $CR^3R^4R^5$ |
|---|---|---|
| 3 | $CH(C_2H_5)C_4H_9$ | $C_2H_5$ |
| 4 | $CH(C_2H_5)C_4H_9$ | $CH(CH_3)_2$ |
| 5 | $CH(C_2H_5)C_4H_9$ | —cyclohexyl (H) |
| 6 | $CH(C_2H_5)C_4H_9$ | —C₆H₄—Cl |
| 7 | $CH(C_2H_5)C_4H_9$ | —(2-thienyl) |
| 8 | $CH(C_2H_5)C_4H_9$ | —(3-thienyl) |
| 9 | $CH(C_2H_5)C_4H_9$ | —(5-F-2-thienyl) |
| 10 | $CH(C_2H_5)C_4H_9$ | —C₆H₄—F |
| 11 | $CH(C_2H_5)C_4H_9$ | —C₆H₄—CF₃ |
| 12 | $CH(C_2H_5)C_4H_9$ | $C_6H_5$ |

TABLE 1-continued

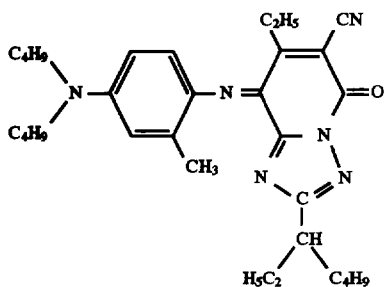

| Ex. No. | R¹ | CR³R⁴R⁵ |
|---|---|---|
| 13 | CH(C₂H₅)C₄H₉ | |
| | | (3-CF₃-phenyl) |
| 14 | CH(C₂H₅)₂ | C₂H₅ |
| 15 | CH(C₂H₅)₂ | CH(CH₃)₂ |

B) Preparation of Dyes

EXAMPLE 16

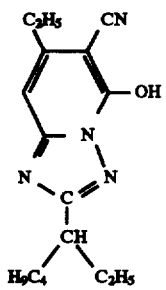

11 g of N,N-dibutyl-m-toluidine were nitrosated with sodium nitrite at from 0° C. to 5° C. in an aqueous hydrochloric acid medium. After 2 hours the mixture was rendered alkaline with 25% strength by weight ammonia water at from 0° to 10° C. and extracted with 150 ml of methylene chloride. The organic phase was subsequently added to a suspension of 14 g of the compound of the formula in acetic anhydride at room temperature with stirring. There was an immediate exothermic reaction. The mixture was subsequently stirred at room temperature for a further 2 hours, heated to 40° C. and admixed with water to hydrolyze acetic anhydride. The organic phase was three times extracted with water and concentrated in a rotary evaporator. The residue was stirred up with water, neutralized with aqueous sodium bicarbonate solution, filtered off with suction, washed neutral and dried at room temperature.

$\lambda_{max}$ (tetrahydrofuran=THF): 614 nm.

The same method was used to obtain the following dyes:

EXAMPLE 17

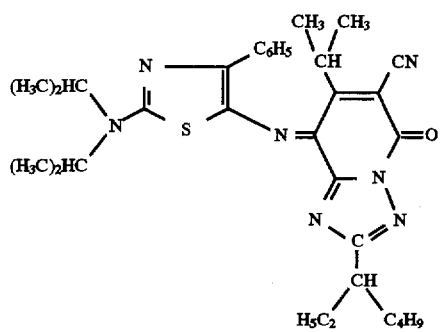

EXAMPLE 18

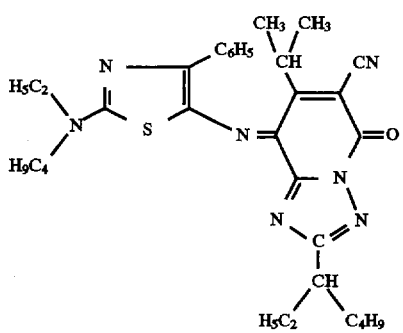

EXAMPLE 19

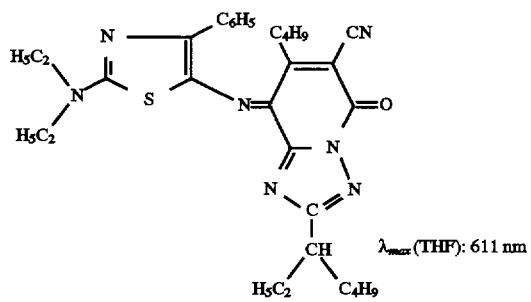

$\lambda_{max}$(THF): 611 nm

EXAMPLE 20

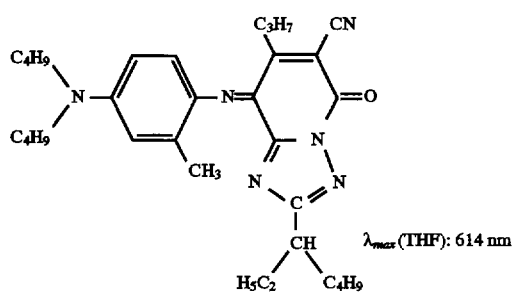

$\lambda_{max}$(THF): 614 nm

EXAMPLE 21

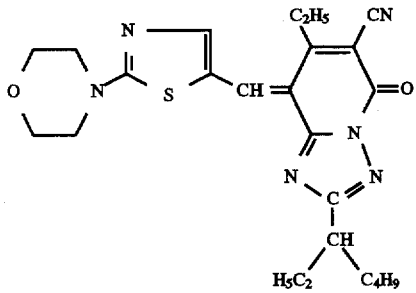

8.3 g of 2-morpholino-5-formylthiazole and 14.0 g of the compound of the formula

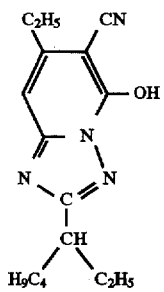

were dissolved in 100 ml of methylene chloride. 100 ml of acetic anhydride were added, methylene chloride was distilled off, and the temperature was raised to 120° C. The mixture was cooled down to 100° C. with stirring to precipitate the target product. 100 ml of methanol were added and the mixture was stirred overnight and filtered with suction, and the filter residue was washed with methanol and dried. $\lambda_{max}$ (THF): 531 nm.

EXAMPLE 22

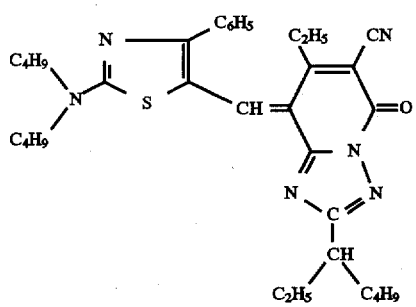

To a solution of 88.4 g (0.31 mol) of the triazolopyridone of the formula

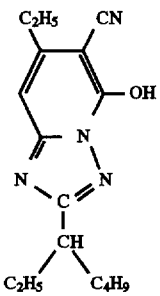

in 438 ml of glacial acetic acid and 438 ml of concentrated hydrochloric acid were added dropwise at from 18° to 20° C. 79 g (0.31 mol) of 27% strength by weight aqueous sodium nitrite solution over 1 h and the mixture was subsequently stirred at room temperature for 2 h. Then 325 ml of water were added at from 18° to 20° C. Then 72 g (0.25 mol) of 2-dibutylamino-4-phenylthiazole were added dropwise at from 18° to 20° C. This was followed by the addition of 438 ml of 25% strength by weight sodium hydroxide solution at a temperature of from 20° to 30° C. so that a pH of not more than 2 was achieved. The suspension dissolved. It was subsequently stirred at 30° C. for 30 min while the pH was corrected once more, so that the value of 2 was maintained. The mixture was then heated to 60° C. and stirred at that temperature for 2 h. It was then cooled down to 50° C. The upper organic phase was then separated from the aqueous phase. The dye oil was dissolved in methanol at 60° C. and made to crystallize by cooling to 10° C. After stirring for one hour the precipitated dye was filtered off with suction. It was then washed with methanol and thereafter with water. The dye was then dried at 60° C. to leave 58.5 g (40%) of dye under reduced pressure (purity 99%).

EXAMPLE 23

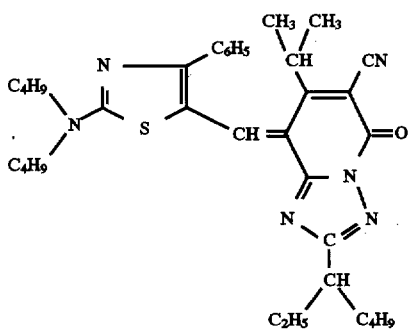

To a solution of 88.4 g (0.31 mol) of the triazolopyridone of the formula

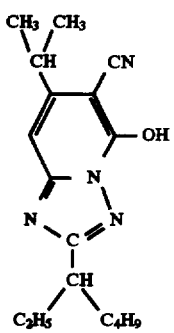

in 438 ml of glacial acetic acid and 438 ml of concentrated hydrochloric acid were added dropwise at from 18° to 20° C. 79 g (0.31 mol) of 27% strength by weight aqueous sodium nitrite solution over 1 h and the mixture was subsequently stirred at room temperature for 2 h. Then 325 ml of water were added at from 18° to 20° C. Then 72 g (0.25 mol) of 2-dibutylamino-4-phenylthiazole were added dropwise at from 18° to 20° C. This was followed by the addition of 438 ml of 25% strength by weight sodium hydroxide solution at a temperature of from 20° to 30° C. so that a pH of not more than 2 was achieved. The suspension dissolved. It was subsequently stirred at 30° C. for 30 min while the pH was corrected once more, so that the value of 2 was maintained. The mixture was then heated to 60° C. and stirred at that temperature for 2 h. It was then cooled down to 50° C. The upper organic phase was then separated from the aqueous phase. The dye oil was dissolved in methanol at 60° C. and made to crystallize by cooling to 10° C. After stirring for one hour the precipitated dye was filtered off with suction. It was then washed with methanol and thereafter with water. The dye was then dried at 60° C. under reduced pressure to leave 48.0 g (30%) of dye (purity 99%).

The same method gives the following dyes:

EXAMPLE 24

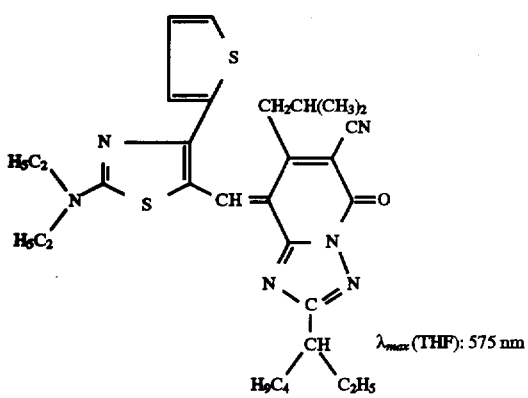

EXAMPLE 25

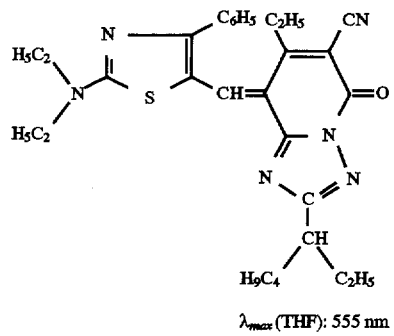

λ_max(THF): 555 nm

EXAMPLE 26

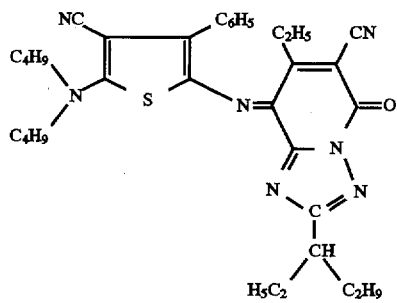

EXAMPLE 27

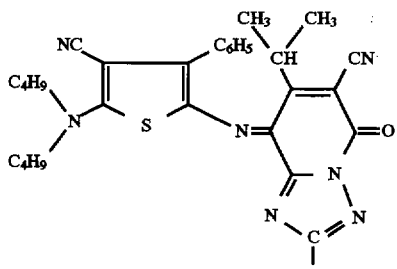

EXAMPLE 28

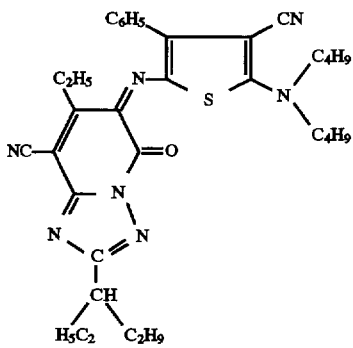

C) Dye Transfer
General Method a) 10 g of dye are stirred, where appropriate with brief heating to 80°–90° C., into 100 g of a 10% by weight solution of a binder based on a linear polyester in a methyl ethyl ketone/toluene/cyclohexanone mixture (4.5:2:2 v/v/v).

The printing ink is applied with a 6 μm knife to a polyester sheet 6 μm thick on whose reverse side a suitable nonstick layer has been applied, and dried with a hair dryer for 1 minute. Before the ink ribbon can be used for printing it must dry in the air for at least 24 hours because residual solvents may impair the printing process.

b) The ink ribbons are used for printing on commercial video-print paper (Hitachi type VY-S) in a computer-controlled test arrangement equipped with a commercial thermal head.

The energy output of the thermal head is controlled by altering the voltage, the pulse duration being set at 7 ms and only one pulse being delivered each time. The energy output is from 0.7 to 2.0 mJ/dot.

Since the level of coloration is directly proportional to the energy supplied, a color wedge can be produced and analyzed spectroscopically.

The Q* (energy in mJ for an absorbance of 1) and the gradient m in 1/mJ are found from the graph of the depth of color against the energy supplied per heating element.

The results are listed below in Table 2.

TABLE 2

| Dye No. | $Q^* \left[\frac{mJ}{dot}\right]$ | $m \left[\frac{1}{mJ}\right]$ |
|---|---|---|
| 16 | 0.98 | 2.48 |
| 19 | 1.01 | 2.30 |
| 20 | 1.02 | 2.60 |
| 25 | 0.94 | 2.51 |

D) Use in Dyeing 10 g of polyester fabric are introduced at 50° C. into 200 ml of a dyeing liquor which contains X% by weight, based on the polyester fabric, of dye and whose pH has been adjusted to 4.5 with acetic acid. After 5 min at 50° C. the liquor temperature was raised over 30 min to 130° C., maintained at that temperature for 60 min and then over 20 min allowed to cool down to 60° C.

Thereafter the dyed polyester fabric is reduction cleared by treating it at 65° C. for 15 min in a 200 ml liquor containing 5 ml/l of 32% strength by weight sodium hydroxide solution, 3 g/l of sodium dithionite and 1 g/l of an addition product of 48 mol of ethylene oxide with 1 mol of castor oil. Finally the fabric is rinsed, neutralized with dilute acetic acid, rinsed once more and dried.

Dye No. 17 was used in an amount (X) of 0.25% by weight. The dyeings obtained were in a very brilliant greenish blue and had excellent fastness to dry heat setting and pleating.

We claim:

1. A triazolopyridine dye of formula I

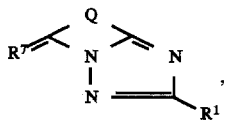

(I)

where $R^1$ is $C_1$–$C_{20}$-alkyl which is unsubstituted or substituted and can be interrupted by 1 to 4 oxygen atoms in ether functionalities, unsubstituted or substituted phenyl, hydroxyl, unsubstituted or substituted $C_1$–$C_{20}$-alkoxy, mercapto or unsubstituted or substituted $C_1$–$C_{20}$-alkylthio, Q is a radical of the formula

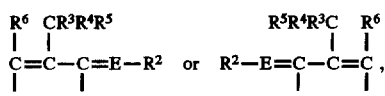

where $R^2$ is a 5- or 6-membered carbocyclic or heterocyclic radical which can be benzo-fused, $R^3$ is hydrogen or unsubstituted or substituted $C_1$–$C_4$-alkyl, $R^4$ is hydrogen, unsubstituted or substituted $C_1$–$C_4$-alkyl or $C_1$–$C_4$-alkoxy, $R^5$ is $C_1$–$C_8$-alkyl which can be interrupted by 1 or 2 oxygen atoms in ether functionalities and can be phenyl- or hydroxyl-substituted, unsubstituted or substituted phenyl, unsubstituted or substituted thienyl or $C_1$–$C_4$-alkoxy which can be interrupted by an oxygen atom in ether functionalities, or the radical $CR^3R^4R^5$ together is $C_3$–$C_7$-cycloalkyl, $C_1$–$C_4$-haloalkyl, unsubstituted or substituted phenyl or unsubstituted or substituted thienyl, $R^6$ is cyano, carbamoyl, carboxyl, $C_1$–$C_4$-alkoxycarbonyl or benzothiazolyl, and E is CH or nitrogen, and $R^7$ is oxygen or a radical of the formula

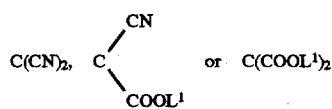

where $L^1$ is in each case $C_1$–$C_8$-alkyl which can be interrupted by 1 or 2 oxygen atoms in ether functionalities, and wherein $CR^3R^4R^5$ is not ethyl.

2. A triazolopyridine dye as claimed in claim 1, wherein $R^6$ is cyano.

3. A triazolopyridine dye as claimed in claim 1, wherein $R^5$ is $C_1$–$C_5$-alkyl or phenyl.

4. A triazolopyridine dye as claimed in claim 1, wherein the radical $CR^3R^4R^5$ together is unsubstituted or substituted phenyl or unsubstituted or substituted thienyl.

5. A triazolopyridine dye as claimed in claim 1, wherein $R^1$ is $C_1$–$C_{13}$-alkyl which is unsubstituted or substituted by $C_1$–$C_6$-alkanoyloxy, $C_1$–$C_8$-alkoxycarbonyl whose alkyl chain can be interrupted by 1 or 2 oxygen atoms in ether functionalities, phenyl or $C_1$–$C_4$-alkylphenyl and which can be interrupted by 1 or 2 oxygen atoms in ether functionalities, or unsubstituted or substituted phenyl.

6. A triazolopyridine dye as claimed in claim 1, wherein $R^2$ is derived from a component of the benzene, indole, quinoline, aminonaphthalene, pyrrole, aminothiazole, benzimidazole, benzothiazole, aminothiophene or diaminopyridine series.

7. A process for transferring dyes from a support to a plastic-coated paper by diffusion or sublimation with the aid of an energy source, which comprises using a support on which there is or are one or more triazolopyridine dyes of the formula I as set forth in claim 1.

8. A method of using the triazolopyridine dyes of claim 1 for dyeing or printing synthetic materials.

9. A triazolopyridine of the formula IV

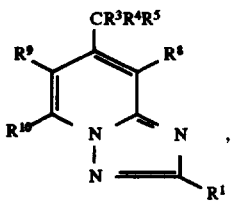

(IV)

where
- $R^1$ is $C_1$–$C_{20}$-alkyl which is unsubstituted or substituted and can be interrupted by 1 to 4 oxygen atoms in ether functionalities, unsubstituted or substituted phenyl, hydroxyl, unsubstituted or substituted $C_1$–$C_{20}$-alkoxy, mercapto or unsubstituted or substituted $C_1$–$C_{20}$-alkylthio,
- $R^3$ is hydrogen or unsubstituted or substituted $C_1$–$C_4$-alkyl,
- $R^4$ is hydrogen or unsubstituted or substituted $C_1$–$C_4$-alkyl or $C_1$–$C_4$-alkoxy,
- $R^5$ is $C_1$–$C_8$-alkyl which can be interrupted by 1 or 2 oxygen atoms in ether functionalities and can be phenyl- or hydroxyl-substituted, unsubstituted or substituted phenyl, unsubstituted or substituted thienyl or $C_1$–$C_4$-alkoxy which can be interrupted by an oxygen atom in ether functionalities, or the radical $CR^4R^4R^5$ together is $C_3$–$C_7$-cycloalkyl, $C_1$–$C_4$-haloalkyl, unsubstituted or substituted phenyl or unsubstituted or substituted thienyl,
- $R^8$ is hydrogen, formyl, nitroso, cyano, $C_1$–$C_4$-alkoxymethyl or a radical of the formula $CH_2$–$NL^2L^3$, where $L^2$ and $L^3$ are each independently of the other hydrogen or $C_1$–$C_4$-alkyl which can be interrupted by $C_1$–$C_4$-alkylimino, or together with the nitrogen atom connecting them are a 5- or 6-membered saturated heterocyclic radical,
- $R^9$ is hydrogen, cyano, carbamoyl, carboxyl, $C_1$–$C_4$-alkoxycarbonyl or benzothiazolyl, and
- $R^{10}$ is hydroxyl, mercapto, halogen, the radical $-NL^2L^3$, where $L^2$ and $L^3$ are each as defined above, or the radical of an acidic—CH compound, and wherein $CR^3R^4R^5$ is not ethyl.

10. A triazolopyridine as claimed in claim 9, wherein one of the two radicals $R^8$ and $R^9$ is hydrogen and the other is cyano.

11. A triazolopyridine as claimed in claim 9, wherein $R^9$ is cyano.

12. A triazolopyridine as claimed in claim 9, wherein $R^9$ is cyano and $R^8$ is hydrogen.

13. A triazolopyridine as claimed in claim 9, wherein $R^5$ is $C_1$–$C_5$-alkyl or phenyl.

14. A triazolopyridine as claimed in claim 9, wherein the radical $CR^3R^4R^5$ is together unsubstituted or substituted phenyl or unsubstituted or substituted thienyl.

15. A triazolopyridine as claimed in claim 9, wherein $R^1$ is $C_1$–$C_{13}$-alkyl or phenyl.

* * * * *